United States Patent
Kaneblei et al.

(10) Patent No.: US 9,778,236 B2
(45) Date of Patent: Oct. 3, 2017

(54) CALIBRATING STATION WITH EXTERNAL GAS ROUTING TRACK

(71) Applicant: Dräger Safety AG & Co. KGaA, Lübeck (DE)

(72) Inventors: Ingo Kaneblei, Lübeck (DE); Stefan Barten, Lübeck (DE)

(73) Assignee: Dräger Safety AG & CO. KGaA, Lübeck (DE)

( * ) Notice: Subject to any disclaimer, the term of this patent is extended or adjusted under 35 U.S.C. 154(b) by 123 days.

(21) Appl. No.: 14/670,727

(22) Filed: Mar. 27, 2015

(65) Prior Publication Data

US 2015/0276695 A1    Oct. 1, 2015

(30) Foreign Application Priority Data

Mar. 29, 2014  (DE) .................. 10 2014 004 618

(51) Int. Cl.
  *G01N 33/00* (2006.01)
(52) U.S. Cl.
  CPC ................. *G01N 33/0006* (2013.01)
(58) Field of Classification Search
  CPC .................. G01N 33/0006; G01N 33/007
  See application file for complete search history.

(56) References Cited

U.S. PATENT DOCUMENTS

| 5,627,328 A * | 5/1997 | Sheridan ............... G01N 1/2258 73/863.83 |
| 7,530,255 B2 * | 5/2009 | Frank .................. G01N 33/0006 73/1.03 |
| 9,255,917 B2 * | 2/2016 | Miyai ................. G01N 33/0006 |
| 2006/0156789 A1 | 7/2006 | Frank et al. |
| 2014/0331737 A1 * | 11/2014 | Kaneblei ........... G01N 33/0006 73/1.06 |

FOREIGN PATENT DOCUMENTS

| DE | 102012008274 A1 * | 5/2013 |
| DE | 10 2012 210 090 A1 | 12/2013 |
| JP | 2006 003 115 A | 1/2006 |

\* cited by examiner

*Primary Examiner* — David A Rogers
(74) *Attorney, Agent, or Firm* — McGlew and Tuttle, P.C.

(57) ABSTRACT

A gas routing element (20) for gassing at least one gas-measuring device (90.1-90.$x$), whereby each gas-measuring device (90.$x$-90.$x$) can be arranged in a test module (30.1-30.$x$) of a calibrating station (100). The gas-measuring devices (90.1-90.$x$) have a first gas inlet opening (1.1-1.$x$), a communicating feed duct (2.1-2.$x$) and a communicating first gas outlet openings (3.1-3.$x$, 13.1-13.$x$). Second gas inlet openings (4.1-4.$x$, 14.1-14.$x$) are connected to a communicating recirculating duct (5.1-5.$x$) and a second gas outlet opening (6.1-6.$x$) is connected with the recirculating duct (5.1-5.$x$) in a gas-communicating manner. A fastening device (70) fastens the gas routing element (20) to the calibrating station (100) or to a test module (30.1-30.$x$) of the calibrating station (100). A calibrating station (100) is also provided for the gas-measuring devices (90.1-90.$x$) with such a gas routing element (20).

20 Claims, 12 Drawing Sheets

CALIBRATING STATION WITH EXTERNAL GAS ROUTING TRACK

CROSS REFERENCE TO RELATED APPLICATIONS

This application claims the benefit of priority under 35 U.S.C. §119 of German Patent Application DE 10 2014 004 618.4 filed Mar. 29, 2014, the entire contents of which are incorporated herein by reference.

FIELD OF THE INVENTION

The present invention pertains to a gas routing element for the gassing of (feeding gas to) at least one gas-measuring device, whereby each gas-measuring device can be arranged in a test module of a calibrating station for gas-measuring devices. Further, the present invention pertains to a calibrating station for gas-measuring devices, having a plurality of test modules, which are arranged in a series to each other, whereby each test module has a mount for the mounting of a gas-measuring device.

BACKGROUND OF THE INVENTION

There are many kinds of portable gas-measuring devices known that have to be carried by persons who spend time in regions, in which they may be exposed to harmful gases. Such portable gas-measuring devices have to be tested regularly for their operability, i.e., whether they react at all to the gas or gases to be detected by them. Besides, such a mere operating test, test gas with a known concentration may also be fed to the gas-measuring device in a so-called calibrating station in order to calibrate the measuring signal of the gas-measuring device.

This means calibrating stations for portable gas-measuring devices are used for testing and adjusting portable gas-measuring devices. The calibrating stations usually have a plurality of modules, so-called test modules, with device-specific mounts for gas-measuring devices. The gassing processes may be directly controlled by the test modules or via a central master module. Gases are fed to the portable gas-measuring devices for the tests and adjustments. Furthermore, the modules also have communication interfaces to exchange data with the portable gas-measuring devices.

Calibrating stations for gas-measuring devices, which need a test gas or calibrating gas and a purge gas, inert gas or zero gas for monitoring the operations and calibrating the gas-measuring devices, are known from the general state of the art.

Such modular-structured calibrating stations are already commercially available. Such a calibrating station for portable gas-measuring devices is known, for example, from the patent application US 2006/0156789 A1. In that case, a plurality of test modules may be coupled to one another in a gas-communicating manner, such that gases can be forwarded from one test module to an adjacent test module. The test modules are, so to say, connected in series, i.e., the portable gas-measuring devices in the respective test modules are correspondingly individually gassed and tested one after the other. This "internal" series connection of the test modules leads, however, to long test times for the portable gas-measuring devices and thus to high costs for the user. Furthermore, besides the connection between adjacent test modules in a gas-communicating manner, it must be ensured that these gas modules are also fixed to one another frictionally in order to be able to reliably maintain the gas-communicating connection permanently.

SUMMARY OF THE INVENTION

An object of the present invention is to at least partly eliminate the above-described drawbacks in the gassing of gas-measuring devices in a modular-structured calibrating station. In particular, an improved and faster gassing and testing of portable gas-measuring devices in a modular-structured calibrating station shall be made possible. Thereby, besides the flexibility of the modular-structured calibrating station, the simple and reliable structure and assembly of the calibrating station shall also especially be prominent.

According to a first aspect of the present invention, the object is accomplished by means of a gas routing element that is suitable for the gassing of at least one gas-measuring device, whereby each gas-measuring device can be arranged in a test module of a calibrating station for gas-measuring devices. According to the present invention, the gas routing element has the following components:

- a first gas inlet opening, a feed duct connected in a gas-communicating manner with the first gas inlet opening and at least two first gas outlet openings connected with the feed duct in a gas-communicating manner,
- at least two second gas inlet openings, a recirculating duct connected in a gas-communicating manner with the second gas inlet openings and a second gas outlet opening connected with the recirculating duct in a gas-communicating manner, as well as
- fastening means for fastening the gas routing element to the calibrating station or a test module of the calibrating station.

For the purpose of the present invention, a gas routing element is comprised not only of simple external hose connections, but is a structurally fixed component, which, as an external component to the test modules, makes possible the parallel feeding of at least one gas and the recirculation of at least one gas, especially spent gas, to and from a plurality of test modules. The gas routing element shifts at least a large part of the gas flow from and to the test modules in the outward direction and thereby makes possible a simpler structure of the test modules. In particular, such a designed gas routing element makes possible a parallel gassing of a plurality of gas-measuring devices in a plurality of test modules in a calibrating station. The size and length of the gas routing element may be or may become adapted to the number of test modules, such that an expandability of a calibrating station to, for example, up to 10 test modules for additional gas-measuring devices is ensured.

Due to the shifting of at least a large part of the gassing, i.e., the gas feeding and the gas exhaust, to the external gas routing element, the gassing times for carrying out the tests of the gas-measuring devices may be kept short. As a result of this, the costs for the testing and adjusting of portable gas-measuring devices in the calibrating station may in turn be kept low.

Furthermore, such a gas routing element makes possible an easy-to-establish, gastight connection among a plurality of test modules for a customer. Depending on how many gas-measuring devices the customer would like to test in the calibrating station at the same time, the size and length of the gas routing element may be adapted to the number of test modules needed. For example, the length and dimension of a gas routing element may be such that three or four test modules and thus gas-measuring devices can be supplied with gas in parallel and too much supplied gas and/or spent gas can be recirculated from the test modules. Should more than four gas-measuring devices be tested at the same time, the gas routing element may have an even longer design.

A further advantage of such an external gas routing element is that a mixing up of lines during the mounting of the calibrating station is ruled out. The test modules preferably have identical designs. These have preset openings for the feeding and discharging of gases. For its part, the gas routing element has openings, via which the gases can be fed and discharged, corresponding to the preset openings in the test modules. Fastening means at the gas routing element ensure that during the fastening of the gas routing element to the test modules, the corresponding openings of the test modules and the openings in the gas routing element are arranged gastightly flush with each other.

The gas routing element has a first gas inlet opening, a feed duct connected in a gas-communicating manner with the first gas inlet opening and at least two first gas outlet openings connected with the feed duct in a gas-communicating manner. By means of this feed duct, fresh gas, for example, can be fed to each of the test modules connected in a gas-communicating manner to the gas routing element. The fresh gas can enter the gas routing element through the first gas inlet opening in order then to be fed to a test module via one of the at least two first gas outlet openings, on the one hand, and, on the other hand, to be forwarded to an additional test module via the at least one second first gas outlet opening. If more than two test modules are supplied with fresh gas via the gas routing element, this element may have the same amount of first gas outlet openings corresponding to the number of test modules. Further, the gas routing element has at least two second gas inlet openings, a recirculating duct connected in a gas-communicating manner with the second gas inlet openings, and a second gas outlet opening connected in a gas-communicating manner with the recirculating duct. This recirculating duct may be used, for example, for recirculating spent test gas. The same amount of second gas inlet openings are provided in the gas routing element corresponding to the number of test modules connected to the gas routing element, whereby a second gas inlet opening is used for the recirculation of spent test gas per test module. The spent test gas in the test modules is then fed via the recirculating duct to the one second gas outlet opening, from where it can be, for example, forwarded via the calibrating station for disposal.

Of course, a gas routing element may also have two or more feed ducts, with a gas inlet opening each and with a plurality of gas outlet openings each corresponding to the number of connected test modules. The same applies to the recirculating duct. A gas routing element may also have two or more recirculating ducts, with a gas inlet opening each and a plurality of gas inlet openings each. Purge gas, inert gas or zero gas may be fed to each connected test module via these additional feed ducts. Correspondingly, the spent or excess residual gases may be recirculated via additional recirculating ducts.

The fastening means of a gas routing element for fastening the gas routing element to the calibrating station or to a test module or a plurality of test modules may have various designs. In particular, the fastening means are designed for frictional fastening. For example, a gas routing element may be fastened by means of screw elements to the calibrating station or to the test modules. Clamping or snap-in connections are also conceivable. As an alternative or in addition, the fastening means may also be designed for positive-locking fastening of the gas routing element to the calibrating station or to a test module or a plurality of test modules. In particular, the fastening means are designed for the secure fastening of a gas routing element to a calibrating station or to one or more test modules. The fastening means may, however, also be designed for the detachable fastening of a gas routing element to a calibrating station or to one or more test modules.

According to a preferred variant of the present invention, provisions may be made in a gas routing element for this element to further have a third gas inlet opening, a third duct connected with the third gas inlet opening in a gas-communicating manner and a third gas outlet opening connected with the third duct in a gas-communicating manner. This third duct may be used, for example, for the recirculation of unneeded test gas to the calibrating station, whereby the test gas is not fed via the gas routing element, but rather directly from test module to test module. For this reason, only a third gas inlet opening is also necessary in the gas routing element for the recirculation of unspent test gas routed through the test modules. Therefore, this third gas inlet opening is preferably arranged at the end of the gas routing element and thus assigned to the last test module arranged in series. The third duct runs correspondingly without additional gas inlet opening over the entire or approximately the entire length of the gas routing element and ends in the third gas outlet opening, from where the unspent test gas can be forwarded to the calibrating station.

Each test module of a calibrating station may be designed such that, for example, test gas may be forwarded directly from one test module to an adjacent test module, without this gas being routed through the gas routing element. As an alternative to this, provisions may advantageously be made in a gas routing element for this element to further have a fourth gas inlet opening, a fourth duct connected with the fourth gas inlet opening in a gas-communicating manner and at least two fourth gas outlet openings connected with the fourth duct in a gas-communicating manner in order to feed, for example, the test gas via the gas routing element to the test modules as well. The gas routing element then has the same amount of fourth gas outlet openings corresponding to the number of test modules of the calibrating station, i.e., one fourth gas outlet opening is provided per connected test module. The test gas may then be fed via the fourth gas inlet opening to the fourth duct of the gas routing element and forwarded from this duct to each of the connected test modules. Such a design of the gas routing element makes it possible that, for example, no gas at all is routed directly from one test module to an additional test module. As a result of this, the structure and assembly of the test modules is simplified.

It is further preferred in a gas routing element, when this is designed as a continuous gas routing module, which is designed for fastening to the calibrating station as well as for the parallel gassing of a plurality of test modules at least via the first gas outlet openings and the second gas inlet openings. The gas routing element may have a different length depending on the number of test modules. If four test modules are provided, for example, the gas routing element is dimensioned such that all four test modules can be gassed in parallel by the one gas routing element. If more than four test modules are connected in series, then the gas routing element is to be dimensioned longer correspondingly.

Moreover, it is particularly advantageous when, in a gas routing element according to the present invention, provisions are made for the gas routing element to have a first gas inlet opening and/or a fourth gas inlet opening as well as a second gas outlet opening and/or a third gas outlet opening for connection with a master module of the calibrating station in a gas-communicating manner. Such a designed gas routing element makes possible the gassing of a plurality of test modules via a master module, i.e., corresponding gases, for example, test gases or fresh gas are provided via the master module that is arranged upstream of the test modules. The gas routing element has corresponding gas inlet openings and gas outlet openings in order to feed the gases provided by the master module to the test modules and to recirculate unspent gases or spent gas from the test modules to the master module. Thus, the gas routing element may have a first gas inlet opening, which can be connected in a gas-communicating manner with a corresponding gas outlet opening of the master module. For example, fresh gas can be fed to the gas routing element and thus to the individual test modules via this connection. Further, a second gas outlet opening may be provided in the gas routing element that can be connected in a gas-communicating manner with a corresponding gas inlet opening of the master module to feed, for example, spent test gas from the test modules back to the master module. Depending on whether gases shall be fed to the test modules via the master module, additional gas inlet openings may be correspondingly provided in the gas routing element. The same applies when additional gases shall be fed from the test modules back to the master module. The gas routing element may correspondingly have additional gas outlet openings, which can be connected in a gas-communicating manner with corresponding gas inlet openings of the master module.

Moreover, it is advantageous when provisions are made in a gas routing element according to the present invention for this element to have a plurality of gas routing modules, whereby each gas routing module has at least one first gas inlet opening and at least one second gas outlet openings to a first additional gas routing module as well as at least one first gas outlet opening and at least one second gas inlet opening to a second additional gas routing module for connecting the gas routing modules with one another in a gas-communicating manner, and whereby each gas routing module has at least one first gas outlet opening and at least one second gas inlet opening for connection in a gas-communicating manner to a test module each. That is, in order to guarantee the expandability of the calibrating station, the external gas routing element may be composed of a plurality of gas routing modules, i.e., sections.

Each gas routing module is designed for the gassing, i.e., feeding and discharging of gases to a test module each. A gas routing module may thereby have exactly the same width and length of a test module. In this way, the gas routing element may be adapted in a simple manner to the number of test modules. Should a calibrating station be expanded by two additional test modules, for example, then the gas routing element may also be correspondingly expanded by adding two additional gas routing modules in order to gas the added test modules. For the purpose of the present invention, to gas or gassing is defined as the feeding and discharging of gases to the respective test modules.

Each gas routing module has at least three gas inlet openings and at least three gas outlet openings. Gas may be fed via a first gas inlet opening to a gas routing module into the feed duct of the gas routing module. Two gas outlet openings branch off from this feed duct. One of the gas outlet openings is used for forwarding the fed gas to a test module, the second gas outlet opening is used for forwarding the gas to an additional gas routing module. Two gas inlet openings and one gas outlet opening are connected to the recirculating duct of the test module. One of the gas inlet openings is used for recirculating gas from the test module into the recirculating duct, the second gas inlet opening is used for recirculating gas that comes from an adjacent gas routing module into the recirculating duct. The recirculated gas or gases may be fed directly or indirectly via a previous gas routing module back to the calibrating station via the gas outlet opening.

A gas routing element, which is composed of a plurality of gas routing modules, may be adapted in a particularly flexible manner to the number of test modules and thus the number of gas-measuring devices to be tested in the test modules. The gas routing element is formed by means of assembling individual gas routing modules. It is consequently possible in a simple and cost-effective manner to assemble just as many gas routing modules as are necessary for the test modules provided. Such a gas routing element assembled from a plurality of gas routing modules makes possible in a simple manner the parallel gassing of a plurality of gas-measuring devices in a plurality of test modules in a calibrating station. Due to the flexible design of the gas routing element, the calibrating station may be expanded by additional test modules, but also be reduced as needed. The gassing time of the individual test modules and of the gas-measuring devices may be kept short due to the external routing of at least some gas lines.

In particular, the individual gas routing modules enable an assembler to easily establish a gastight connection among a plurality of test modules. It is thereby particularly advantageous when at first the test modules are fastened to one another and subsequently the gas routing element as a whole is connected to the test modules in a gas-communicating manner. Consequently, a false connection of the gas routing element or of the gas routing modules to the test module or to the test modules can especially be prevented, i.e., the gas routing element can be configured externally without problems and can be adapted to the different number of test modules. A mixing up of lines is especially ruled out by such a gas routing element. Further, it is advantageous in such a gas routing element when the gas routing modules can no longer be individually separated after the gas routing element has been mounted on the test modules. Consequently, a simple breaking of the gas connection via the gas routing element can be prevented. The gas routing element may hence preferably be designed in connection with the test modules, such that this can be connected only as a whole to the test modules and again be separated from these test modules.

A further advantage of the modular structure of the gas routing element by means of a plurality of individual gas routing modules is that defective gas routing modules can be replaced. It is then not necessary to replace the entire gas routing element.

According to a particularly preferred variant of the present invention, provisions may be made in a gas routing element for this element to have a gas routing master module to the calibrating station, especially to a master module of the calibrating station, whereby the gas routing master module has at least two gas inlet openings, at least two gas outlet openings as well as at least one feed duct and at least one recirculating duct for connecting a gas inlet opening each with a gas outlet opening in a gas-communicating manner.

The gas routing master module may be designed, such that this gas routing master module can establish both a connection in a gas-communicating manner to a master module of the calibrating station and a connection in a gas-communicating manner to the first test module fastened to the master module. In this case, the gas routing master module covers both the master module of the calibrating station and a test module and thereby has a greater width and length than the additional gas routing modules, which have each the width and length of a test module. The gas routing module thus forwards gases directly to the first test module connected to the master module. At the same time, the gas routing master module establishes the connection to the master module for the recirculation of gases from the test modules.

Especially preferably, the gas routing master module is assigned only to the master module and not directly to a test module, however. Such a gas routing master module is designed for connecting the master module in a gas-communicating manner to a first gas routing module of a test module, i.e., the gas routing master module represents the first component of the gas routing element. To form the gas routing element, a plurality of gas routing modules may be connected to the gas routing master module. The gas routing master module thus represents the connecting piece among the gas routing modules of the test modules and of the calibrating station, in particular a master module of the calibrating station. The number of gas inlet openings, gas ducts and gas outlet openings of the gas routing master module are correspondingly adapted to the number of gas inlet openings, gas ducts and gas outlet openings of the gas routing modules. Thus, at least one gas, for example, fresh gas and/or test gas, can be routed via the gas routing master module to the gas routing modules connected in series and thus to the test modules. Further, at least one gas, for example, unspent test gas and/or spent test gas, can be routed via the gas routing modules back to the gas routing master module and thus back to the calibrating station.

A further advantage of an above-mentioned gas routing element is that this gas routing element is an integrative component of the calibrating station after the mounting on the calibrating station, in particular on the test modules. This leads to high safety of the gas routing and stability of the entire unit. The possibilities of error in the installation of the entire unit are reduced.

Moreover, it is advantageous when provisions are made in a gas routing element according to the present invention for the sealing elements, especially O-ring seals, to be provided for the gastight connection of the gas routing element to the calibrating station, in particular to a master module and the test modules of the calibrating station, or between two adjacent gas routing modules at the gas inlet openings and the gas outlet openings, i.e., in order to guarantee the tightness of the external gas routing element to the master module and/or to the test modules as well as to one another, the gas routing element is or the gas routing modules are connected via O-rings in a gastight manner. It is especially advantageous when components made of fluorinated rubber are used for the gastight connection between the external gas routing element and the master module or the test modules in the area of the openings, and especially around the openings. These components may be designed as a sealing profile, for example, as an O-ring. A known fluorinated rubber is, for example, Viton® from the firm of DuPont.

For example, components made of fluorinated rubber in the direction of the external gas routing track may be designed as a sealing profile, for example, as an O-ring. In the direction of the master module or the test modules, these components may be designed as hose liners in order to be able to connect the gas-routing elements in the interior of the master module or of the test modules with the external gas routing element.

It may be further advantageous when in a gas routing element according to the present invention, at least one locking mechanism is provided for positioning the gas routing element at the calibrating station and/or when the gas routing modules and the gas routing master module have fastening elements for fastening to one another. The at least one locking mechanism, for example, plug-in elements, prevents an incorrect mounting sequence of the gas routing element and of the calibrating station or the test modules. The calibrating station and the test modules advantageously also have locking countermechanisms, for example, mounts for plug-in elements. The at least one locking mechanism guarantees that the master module and test modules have to be mounted first and then the gas routing element is mounted as a whole onto the calibrating station, i.e., the master module and the test modules. For removal, for example, in the event of a defective test module, the at least one locking mechanism guarantees that the gas routing element must be removed first and then the master module and the test modules can be removed. The locking mechanism may be designed, for example, as a crossrib in the gas routing element, especially in the individual gas routing modules of the gas routing element, which mesh with corresponding openings in the master module and the test modules. Via these crossribs, individual test modules or the master module and the test module adjacent to the master module are prevented from being able to be pulled apart from one another. This increases the reliability of the calibrating station.

Fastening elements at the gas routing modules or the gas routing master module guarantee that these can be fastened to one another rigidly and reliably in a gas-communicating manner and especially in a gastight manner. These fastening elements guarantee a high stability of the gas routing element even in large configurations, i.e., of a high number of gas routing modules. Preferably, the gas routing modules and the gas routing master module have positive-locking fastening elements, e.g., locking hooks and locking hook mounts.

It is possible to achieve a further advantage when in a gas routing element according to the present invention it has a closing element for closing the ducts, i.e., the at least one feed duct, the at least one recirculating duct and/or the at least one third and fourth duct, of the gas routing element and/or for connecting at least the fourth duct of a test module in a gas-communicating manner with the gas routing element. The closing element closes the end of the gas routing element and the "last" gas routing module at least partially. If, for example, gas is directly transmitted from a test module to an adjacent test module, then the closing element is used for forwarding the gas routed through the "last" test module to the gas routing element to feed this back to the master module. Then, the closing element may have openings and ducts for the recirculation of gases, for example, unspent test gas, from the test modules to the gas routing element. Also, the closing element advantageously has sealing elements, in particular O-ring seals made of fluorinated rubber. Further, the closing element may have at least one locking mechanism for positioning the closing element at the end of the gas routing element, in particular the "last" gas routing module, and at the "last" test module fastened in the series. In addition or as an alternative to the locking mechanism, the closing element may have fastening elements for the fastening of the closing element to the gas routing element, in particular, to the "last" gas routing module, and to the "last" test module fastened in the series.

According to a second aspect of the present invention, the object is accomplished by a calibrating station for gas-measuring devices, having a plurality of test modules, which are arranged in a series with one another, whereby each test module has a mount for a gas-measuring device. The calibrating station is characterized in that it has a gas routing element according to the first aspect of the present invention, in particular in accordance with one of the claims 1 through 10 for gassing the gas-measuring devices in the mounts of the test modules, and in that the test modules have test module openings for connecting the test modules in a gas-communicating manner with the gas routing element, in particular the first gas inlet openings and the second gas inlet openings of the gas routing element. The test modules have corresponding lines to feed fed gases, excess gases and/or spent gases through the test modules. In particular, the lines in the test modules are designed such that the respective gas-measuring device located in a mount of a test module can be gassed.

The lines of a test module preferably run such that gases can only be fed from the gas routing element and be fed back to the gas routing element. However, it is also conceivable that at least one line within the test modules runs such that at least one gas can be fed directly from one test module to an adjacent second test module.

The test module openings of the test modules are designed and arranged such that these are able to establish a gas-communicating connection to the first gas outlet openings and the second gas inlet openings of the gas routing element, in particular the individual gas routing modules. As a result of this, for example, gas can be fed via the feed duct and the first gas outlet openings of the gas routing element or via the feed ducts and the first gas outlet openings of the gas routing modules to the respective test modules. Further, for example, spent gas or unspent gas in the test modules may be fed from the test modules via the second gas inlet openings of the gas routing element or of the individual gas routing modules back into the gas routing element.

Such a designed calibrating station has a plurality of advantages over the conventional calibrating stations. The gassing times for gassing gas-measuring devices can be markedly reduced, since a parallel gassing of a plurality of gas-measuring devices can be carried out by means of the at least mostly external gas routing through the gas routing element, i.e., the carrying out of tests of the gas-measuring devices can be kept short in such a calibrating station. Further, the costs for testing and adjusting the portable gas-measuring devices can thereby be kept low.

A particular advantage of such a calibrating station lies in the fact that the gas routing element can be adapted flexibly to the number of the gas-measuring devices to be tested. In particular, such a calibrating station makes possible an easy-to-establish gastight connection among a plurality of test modules for the customer. Depending on how many gas-measuring devices the customer would like to test in the calibrating station at the same time, the size and length of the gas routing element can be adapted to the number of test modules needed.

According to one embodiment of the calibrating station, the gas routing element may be a single component, which can be connected in a gas-communicating manner to a plurality of test modules. The length and dimension of the gas routing element then depends on the number of test modules. In the preferred embodiment of a calibrating station, the gas routing element is, however, formed by a plurality of gas routing modules that can be assembled. Consequently, a customer can assemble the gas routing element in a flexible manner and adapt it to his own needs, i.e., depending on the number of gas-measuring devices to be tested and thus on the number of test modules assembled in a series. Consequently, the length of the gas routing element can be easily individually adapted to the length and number of the test modules. In particular, costs can be thereby saved. The customer always needs only to add so many gas routing modules to a gas routing element as needed.

A further advantage of such a calibrating station is that a mixing up of lines during the mounting of the calibrating station is ruled out. The test modules preferably have identical structures. These test modules have preset test module openings for feeding and discharging gases. The gas routing element in turn has openings, via which gases can be fed to and discharged from the test modules, corresponding to the preset test module openings in the test modules. Fastening elements at the gas routing element and the gas routing modules ensure that when fastening the gas routing element and the gas routing modules to the test modules, the corresponding test module openings of the test modules and the openings, i.e., the gas inlet openings and the gas outlet openings in the gas routing element can be arranged flush with one another in a gastight manner.

The fastening elements and the at least one locking mechanism of the gas routing element and of the gas routing modules are preferably designed in connection with corresponding fastening elements and locking countermechanisms of the test modules, such that for mounting the calibrating station, first the test modules must be fastened to one another, then the gas routing modules and optionally the gas routing master module must be joined to one another and only then is the joined gas routing element as a whole fastened to the joined test modules. As a result of this, the calibrating station is mounted in a particularly reliable manner. Both the gas routing modules and test modules can thus no longer be individually separated from the calibrating station after the mounting of the gastight connection. Nevertheless, it is possible to replace defective gas routing modules or test modules by the calibrating station being completely disassembled.

It is further advantageous when provisions are made in a calibrating station according to the present invention for the calibrating station to have a master module for controlling the gassing of the calibrating station, whereby the master module has a fresh gas inlet, a fresh gas line and a fresh gas outlet for feeding fresh gas to the test modules, at least one test gas inlet, at least one test gas line as well as at least one test gas outlet for feeding at least one test gas to the test modules, a first waste gas inlet, a first waste gas line and a first waste gas outlet for recirculating spent test gas from the test modules through the master module as well as a second waste gas inlet, a second waste gas line and a second waste gas outlet for recirculating unspent test gas from the test modules through the master module. Such a designed calibrating station makes possible the feeding of test gas and fresh gas to the gas-measuring devices for testing the said gas-measuring devices. At the same time, the calibrating station also makes possible the recirculation of spent and unspent test gas to the master module. The master module can thereby control, in particular control or regulate, the pressure and the speed, with which the gases are routed through the corresponding ducts and lines. Further, the master module can control, by means of switches in the master module, which test gas is fed to the test modules and thus to the gas-measuring devices in the mounts of the test modules. Thereby, in particular, the at least one test gas line can feed at least one test gas directly to the first test module fastened to the master module or indirectly via the gas routing element to all the test modules at the same time. The master module can be connected to corresponding gas sources. Further, the master module may be connected to gas disposal sites in order to dispose of spent or unspent gas in an environmentally responsible way.

The length and dimension of the gas routing element may be different. Preferably, the length of the gas routing element can, however, be adapted to the number and size of the test modules. One gas routing module is especially preferably provided per test module, i.e., the gas routing element may be flexibly adapted to the test modules, in particular to the number of test modules, by adding gas routing modules. Especially preferably, a gas routing module has the same length and width of a test module, such that a gas routing module can be assigned exactly to one test module. This means a gas routing module then correspondingly has all test module openings that are needed for gassing a test module. Further, a gas routing module has gas outlet openings in order to forward gases to an adjacent gas routing module or to take up gases from an adjacent gas routing module and to feed them back to the master module.

It is also advantageous when provisions are made in a calibrating station according to the present invention for the feed duct of the gas routing element to be designed for feeding fresh gas to the test modules, the fourth duct to be designed for feeding test gas to the test modules, for the recirculating duct to be designed for recirculating spent test gas from the test modules, and for the third duct to be designed for recirculating unspent test gas from the test modules. This represents a particularly preferred embodiment of a gas routing element. In such a designed gas routing element, all gases needed for testing the gas-measuring devices may be fed via the gas routing element. No direct connections between two adjacent test modules in a gas-communicating manner are needed in such a gas routing element. The test modules can be manufactured in a simple and cost-effective manner as a result of this. A gastight sealing of the gas openings of the test modules is only necessary in the direction of the gas routing element, but not to adjacent test modules. If the gas routing element is formed by two or more gas routing modules, then the above-mentioned ducts refer each to a gas routing module, i.e., each gas routing module then has ducts of such a design.

According to another preferred variant of the present invention, provisions may also be made in a calibrating station for the test modules to have each a test gas inlet opening, a test gas duct and a test gas outlet opening for feeding test gas to the test modules, whereby the test gas outlet opening of a test module can be connected in a gas-communicating manner with the test gas inlet opening of an adjacent test module. In such an embodiment of the test modules, test gas can be forwarded directly from test module to test module. A feeding of test gas to the gas-measuring devices via the gas routing element is not necessary in this case. However, the feeding of fresh gas to the test modules may continue to take place via the gas routing element. The same applies to the recirculation of spent test gas. This may also take place via the gas routing element and the gas routing modules assigned to the test modules. A closing element may be fastened in a gas-communicating manner to the last test module connected in a series in order to discharge the unspent test gas. Therefore, the closing element preferably has one duct and one gas outlet opening, which can be connected in a gas-communicating manner with the gas routing element.

It is further advantageous when in a calibrating station according to the present invention, sealing elements, in particular O-ring seals, are provided for the gastight connection of the test modules to the gas routing element and/or to the master module and between the master module and the gas routing element to the test module openings, the fresh gas outlet, the test gas outlet, the first waste gas inlet and the second waste gas inlet. These guarantee the sealing of the test modules to the gas routing element, of the master module to the gas routing element, of the master module to a test module and between the test modules. It is particularly advantageous when the sealing elements have components made of fluorinated rubber for the gastight sealing. These may be designed as sealing profiles, for example, as O-rings.

It may be advantageous when in a calibrating station according to the present invention the master module has a compressed air inlet and a compressed air line, whereby the compressed air line is connected in a gas-communicating manner via a switch with the fresh gas line. As a result of this, compressed air can be conducted through all components of the calibrating station. In particular, the ducts of the gas routing element, but also those of the test modules can be cleaned by feeding compressed air, i.e., besides the inlets for the test gas, the master module may also have an inlet for compressed air. The master module may have a compressed air pump as well. The master module may be designed such that it is possible to switch back and forth between the inlet for fresh air and the compressed air pump. The compressed air or fresh air is needed for purging the gas-measuring devices after a gassing by means of test gas, among other things. The compressed air or fresh air is switched to a fresh gas line in the master module. This fresh gas line is fed from the master module via the feed duct of the external gas routing element to the test modules. In the external gas routing element, the feed duct is designed as a continuous line. Further, the feed duct has branches for feeding fresh gas to each test module. As an alternative or in addition to the compressed air pump, the master module may have a fresh air pump.

Especially preferred is a calibrating station, in which the test module openings of the test modules, the gas inlet openings and gas outlet openings of the gas routing element and/or the fresh gas inlet, the fresh gas outlet, the test gas inlets, the test gas outlet, the first waste gas inlet, the first waste gas outlet, the second waste gas inlet and the second waste gas outlet of the master module are designed as sealing, plug-type connecting elements. The plug-type connecting elements may be designed as plugs, male part, or as plug mounts, female part. In particular, two plug-type connecting elements may be connected gastightly with one another by means of a positive locking. In addition, the above-described sealing elements may be provided at the plug-type connecting elements.

Moreover, it is advantageous when in a calibrating station according to the present invention the test modules and/or the master module have locking countermechanisms for positioning the gas routing element at the calibrating station. These locking countermechanisms, in coordination with the at least one locking mechanism of the gas routing element, provide for an exact positioning of the gas routing element at the test modules or at the master module. By means of this exact positioning, a gastight connection of the gas-communicating gas inlet and gas outlet openings of the components of the calibrating station is guaranteed. The locking countermechanisms may be designed, for example, as mounts for locking mechanisms, designed as crossribs, of the gas routing element, in particular of the gas routing modules. Individual test modules and the master module are prevented from being able to be pulled apart from one another via the locking countermechanisms and the locking mechanisms. This increases the reliability of the calibrating station. Therefore, it may be further advantageous when in a calibrating station according to the present invention the gas routing modules, the gas routing master module, the master module and the test modules are designed and coordinated with one another such that the gas routing modules and the gas routing master module can only be fastened in a gas-communicating manner to the master module and to the test modules in the assembled state.

Features and details, which are described in connection with one aspect of the present invention, are also valid in connection with any other aspect of the present invention as well as vice versa and alternately, such that reference is and can always be made mutually to the individual aspects of the present invention with regard to the disclosure. Further advantages, features and details of the present invention appear from the description below, in which exemplary embodiments of the present invention are described in detail with reference to the drawings. Thereby, each of the features mentioned in the claims and in the description may be essential to the present invention individually by itself or in any combination. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
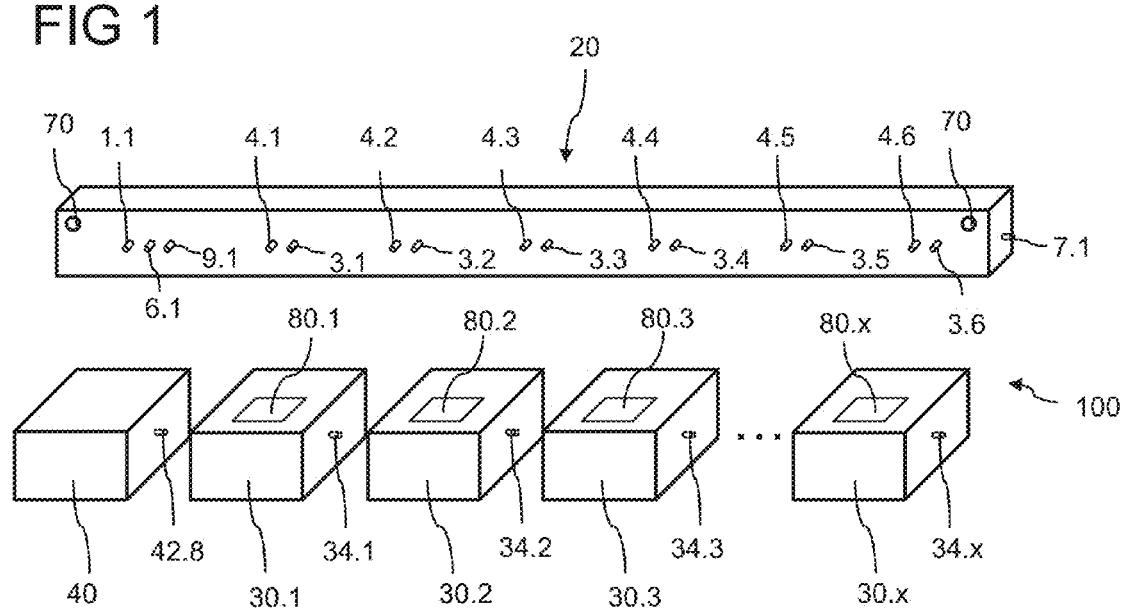
FIG. 1 is a schematic view showing a gas routing element, a master module as well as a plurality of test modules of a first calibrating station according to the present invention.

Referring to the drawings, exemplary embodiments of the present invention are described below in detail on the basis of the attached drawings. Here, identical components are each provided with the same reference numbers of a plurality of figures. The components and features, purposes and effects, which are described in reference to an exemplary embodiment, insofar as not expressly or obviously ruled out, are assumed to be applicable in any other exemplary embodiment and shall also apply as disclosed in reference to the respective other exemplary embodiment even if they are not expressly shown and/or described there. Further, it is apparent that the drawings are defined as schematic and no limitations shall be taken from them with respect to concrete dimensions or size ratios, unless this is expressly so described.

FIG. 1 schematically shows a gas routing element 20, a master module 40 as well as a plurality of test modules 30.1 through 30.x of a first calibrating station 100 according to the present invention. The gas routing element 20 has a one-part design and is used for the parallel gassing of the plurality of test modules 30.1 through 30.x. The test modules 30.1 through 30.x have mounts 80.1 through 80.x each for gas-measuring devices 90.1 through 90.x. When gas-measuring devices 90.1 through 90.x are arranged in the mounts 80.1 through 80.x, these can be tested for their operability in the calibrating station 100. The gas routing element 20 has a first gas inlet opening 1.1, a second gas outlet opening 6.1 as well as a third gas outlet opening 9.1, which are used to connect the gas routing element 20 in a gas-communicating manner with the master module 40. Further, the gas routing element 20 has a plurality of first gas outlet openings 3.1 through 3.x as well as a plurality of second gas inlet openings 4.1 through 4.x, which are used to connect the gas routing element 20 in a gas-communicating manner with the test modules 30.1 through 30.x. Correspondingly, a feed duct 2.1 as well as a recirculating duct 5.1 are arranged in the gas routing element 20, i.e., gas, for example, fresh gas, may be fed starting from the master module 40 via the gas inlet opening 1.1 to the feed duct 2.1 of the gas routing element 20. The gas is fed at the same time to the individual test modules 30.1 through 30.x via the feed duct 2.1 and the gas outlet openings 3.1 through 3.x of the gas routing element 20. The test modules 30.1 through 30.x further have test module openings 34.1 through 34.x for the gas-communicating connection of the test modules 30.1 through 30.x with one another. Thus, a gas, for example, test gas, can be fed directly to the test modules 30.1 through 30.x via a corresponding test gas outlet 42.8 of the master module 40. The feeding of this gas does not take place via the gas routing element 20. The gas routing element 20 has a third duct 8.1, via which gas exiting from the test module opening 34.x of the last test module 30.*x*, especially unspent test gas, can be fed back. The access to the third duct 8.1 takes place via the gas inlet opening 7.1 of the gas routing element 20. The length of the gas routing element 20 is adapted correspondingly to the plurality of the test modules 30.1 through 30.*x*. The more test modules 30.1 through 30.*x* are arranged in series to one another, the longer is the gas routing element 20. If, for example, only three test modules 30.1 through 30.*x* are connected to the master module 40, then a long gas routing element 20 may be used versus a shorter gas routing element 20 with first gas outlet openings 3.1 through 3.3 and second gas inlet openings 4.1 through 4.3 for only three test modules 30.1 through 30.3.

Figure 2:
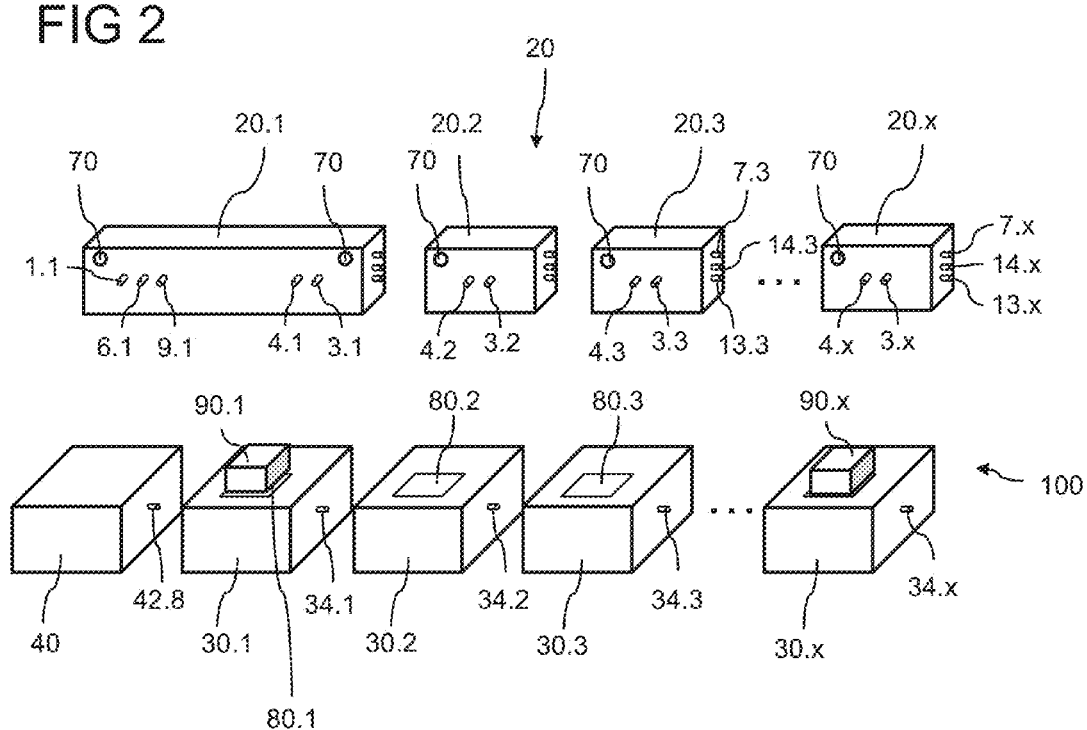
FIG. 2 is a schematic view showing a gas routing element having a plurality of gas routing modules, a master module as well as a plurality of test modules of a second calibrating station according to the present invention.

FIG. 2 schematically shows a gas routing element 20 having a plurality of gas routing modules 20.1 through 20.*x*, a master module 40 as well as a plurality of test modules 30.1 through 30.*x* of a second calibrating station 100 according to the present invention. The first gas routing module 20.1 has a dual function and therefore has a different design than the remaining gas routing modules 20.2 through 20.*x*. The first gas routing module 20.1 is used, on the one hand, for connecting the gas routing element 20 to the master module 40. Further, the first gas routing module 20.1 is used for connecting the gas routing element 20 to the first test module 30.1 in a gas-communicating manner. The additional gas routing modules 20.*x* through 20.*x* are adapted correspondingly to the additional test modules 30.2 through 30.*x* on same. A gas-measuring device 90.1 or 90.*x* each is connected in the mounts 80.1 and 80.*x* of the first test module 30.1 or the last test module 30.*x*, respectively. The mounts 80.1 through 80.*x* are designed such that gases can be routed from and to the gas-measuring device 90.1 through 90.*x* located in the mounts 80.1 through 80.*x* in order to test this gas-measuring device for operability thereof. The third gas inlet openings 7.1 through 7.*x*, the first gas outlet openings 13.1 through 13.*x* as well as the second gas inlet openings 14.1 through 14.*x* of the individual gas routing modules 20.1 through 20.*x* are shown in FIG. 2.

Figure 3:
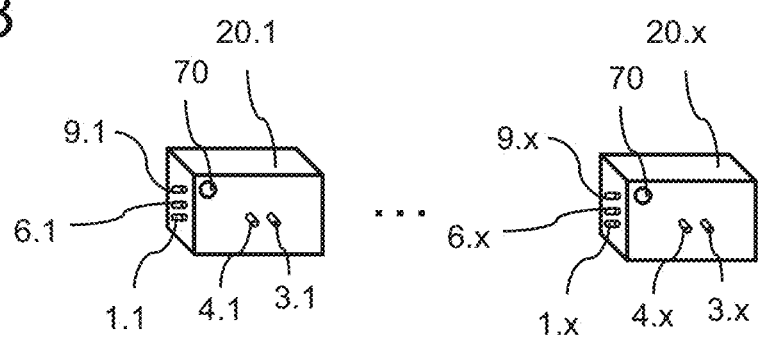
FIG. 3 is a schematic view showing gas routing modules of a gas routing element of a third calibrating station according to the present invention.
Figure 4:
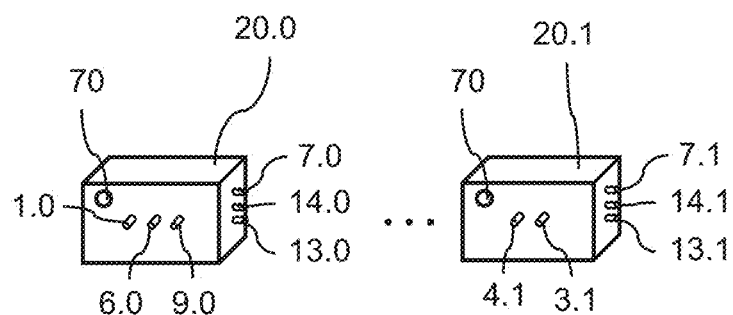
FIG. 4 is a schematic view showing a gas routing master module as well as gas routing modules of a gas routing element of the third calibrating station according to the present invention.

FIGS. 3 and 4 schematically show different perspective views of gas routing modules 20.1 through 20.*x* of a gas routing element 20 of a third calibrating station 100 according to the present invention. In addition, a gas routing master module 20.0 is shown in FIG. 4. Each gas routing module 20.1 through 20.*x* has a first gas inlet opening 1.1 through 1.*x*, two first gas outlet openings 3.1 through 3.*x* and 13.1 through 13.*x* connected in a gas-communicating manner with a feed duct 2.1 through 2.*x*, not shown. Furthermore, each gas routing module 20.1 through 20.*x* has two second gas inlet openings 4.1 through 4.*x* and 14.1 through 14.*x*, a recirculating duct 5.1 through 5.*x*, not shown, connected in a gas-communicating manner with the second gas inlet openings 4.1 through 4.*x* and 14.1 through 14.*x*, as well as a second gas outlet opening 6.1 through 6.*x* connected in a gas-communicating manner with the recirculating duct 5.1 through 5.*x*. Also, each gas routing module 20.1 through 20.*x* has a third gas inlet opening 7.1 through 7.*x*, a third duct 8.1 through 8.*x*, not shown, connected in a gas-communicating manner with the third gas inlet opening 7.1 through 7.*x* and a third gas outlet opening 9.1 through 9.*x* connected in a gas-communicating manner with the third duct 8.1 through 8.*x*. The gas routing master module 20.0 has corresponding openings and ducts.

The gas routing element 20 can be fastened via fastening means 70 to the master module 40 as well as to the test modules 30.1 through 30.*x*, see FIGS. 1 through 4. For example, the fastening means 70 may be holes, especially threaded holes, in the gas routing element 20, through which fastening screws can be passed and screwed into corresponding holes in the master module 40 as well as in the test modules 30.1 through 30.*x*. The gas routing element 20 preferably has two or more holes 70, in particular one hole 70 for each module 40, 30.1 through 30.*x*. The fastening means 70 at the gas routing element 20 ensure that when fastening the gas routing element 20 to the master module 40 as well as to the test modules 30.1 through 30.*x*, the corresponding openings 32.1 through 32.*x*, 33.1 through 33.*x* of the test modules 30.1 through 30.*x* as well as the corresponding openings 41.3, 43.1, 44.1 of the master module 40 and the respective, corresponding openings 1.1 through 1.*x*, 6.0 through 6.*x*, 9.0 through 9.*x* as well as 3.1 through 3.*x* and 4.1 through 4.*x* of the gas routing element 20 are arranged gastightly flush with one another. In particular, the fastening means 70 are designed for frictional fastening. Besides holes 70 and screw elements, clamping or snap-in connections are also conceivable. As an alternative or in addition, the fastening means 70 may also be designed for the positive-locking fastening of the gas routing element 20 to the calibrating station 100 or to a test module 30.1 or a plurality of test modules 30.1 through 30.*x*.

Figure 5:
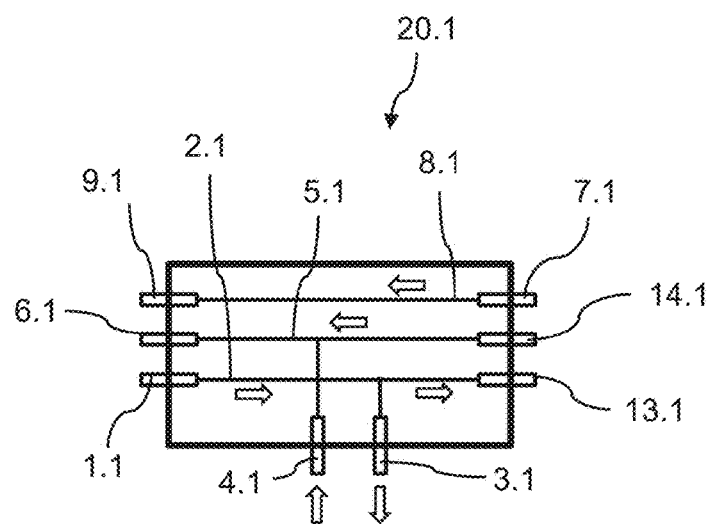
FIG. 5 is a schematic view showing a gas routing module of a first gas routing element.

FIG. 5 schematically shows the gas routing module 20.1 according to FIGS. 3 and 4 in a different manner of representation. In addition to the gas inlet openings and gas outlet openings, the feed duct 2.1, the recirculating duct 5.1 as well as the third duct 8.1 of the gas routing module 20.1 are shown. For example, fresh gas can be fed through the first gas inlet openings 1.1 through 1.*x* from a master module 40 into the feed ducts 2.1 through 2.*x*, not shown. The feed ducts 2.1 through 2.*x* of the respective gas routing modules 20.1 through 20.*x* feed the fresh gas, on the one hand, via the first gas outlet openings 3.1 through 3.*x* to the test modules 30.1 through 30.*x*, and, on the other hand, they feed the fresh gas from one test module 30.1 through 30.*x* to the next test module 30.1 through 30.*x*. Spent test gas can be fed via the two second gas inlet openings 4.1 through 4.*x* and 14.1 through 14.*x* from the test modules 30.1 through 30.*x* into the recirculating ducts 5.1 through 5.*x*. The spent test gas is fed via the second gas outlet openings 6.1 through 6.*x* from gas routing module 20.1 through 20.*x* to gas routing module 20.1 through 20.*x* and finally via the gas routing master module 20.0 back to the master module 40. The third duct 8.1 through 8.*x* of each gas routing module 20.1 through 20.*x* connects the third gas inlet openings 7.1 through 7.*x* in a gas-communicating manner with the third gas outlet openings 9.1 through 9.*x*. Unspent test gas can be fed via these third ducts 8.1 through 8.*x* into the test modules 30.1 through 30.*x* back to the master module 40. Arrows at the ducts 2.1, 5.1 and 8.1 indicate the flow directions of the gases flowing into the ducts 2.1, 5.1 and 8.1.

Figure 6:
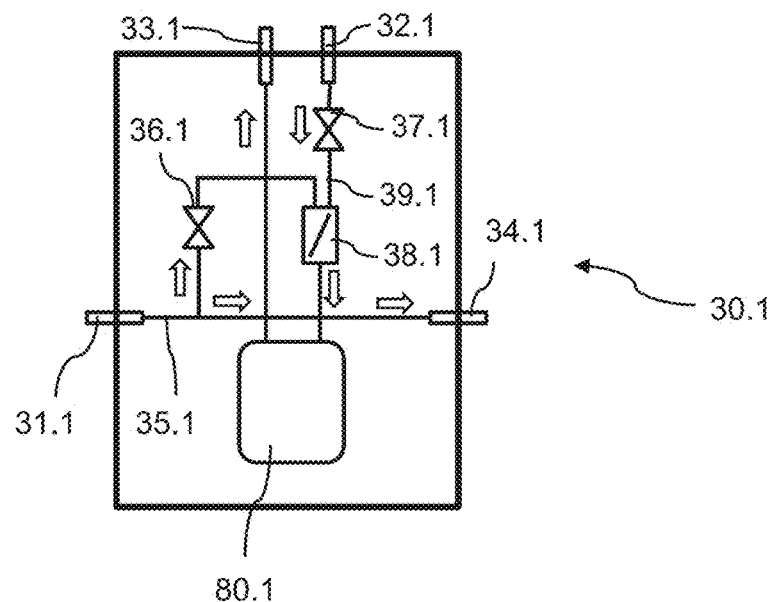
FIG. 6 is a schematic view showing a first test module belonging to the gas routing module according to FIG. 5.

FIG. 6 schematically shows the test module 30.1 assigned to the gas routing module 20.1 shown in FIG. 5. This test module has two test module openings 32.1 and 33.1 for connecting to the gas routing module 20.1 in a gas-communicating manner whereby gas, especially fresh gas, can be fed via the test module opening 32.1 to the test module 30.1, and gas, especially spent test gas, can be fed via the test module opening 33.1 from the test module 30.1 to the gas routing module 20.1. Further, the test module 30.1 has a third test module opening 31.1 for feeding test gas directly from the master module 40 or from another test module 30.2 through 30.*x*, arranged upstream, as well as a fourth test module opening 34.1 for forwarding unspent test gas to a test module 30.2 through 30.*x* arranged downstream. A part of the test gas introduced is fed through the test gas duct 35.1 of the mount 80.1, while a second, especially larger part of the test gas is fed further to the test gas outlet opening 34.1 for forwarding to a next test module 30.2. A valve device 36.1 is arranged in the test gas duct 35.1 for the accurate metering of the test gas fed to the mount 80.1. Further, a switching device 38.1, which is designed to switch back and forth between the test gas duct 35.1 and a fresh gas duct 39.1, may be provided in the test gas duct 35.1, which is fed to the mount 80.1. A valve device 38.1 may also be arranged in the fresh gas duct 39.1 for metering the fed fresh gas. The test gas or fresh gas may be fed into the gas-measuring device lying in the mount 80.1 to test or purge this gas. The spent test gas or the fresh gas passed through is forwarded via an additional line of the test module opening 33.1, from where it is discharged via the recirculating duct 3.0 through 3.1.

Figure 7:
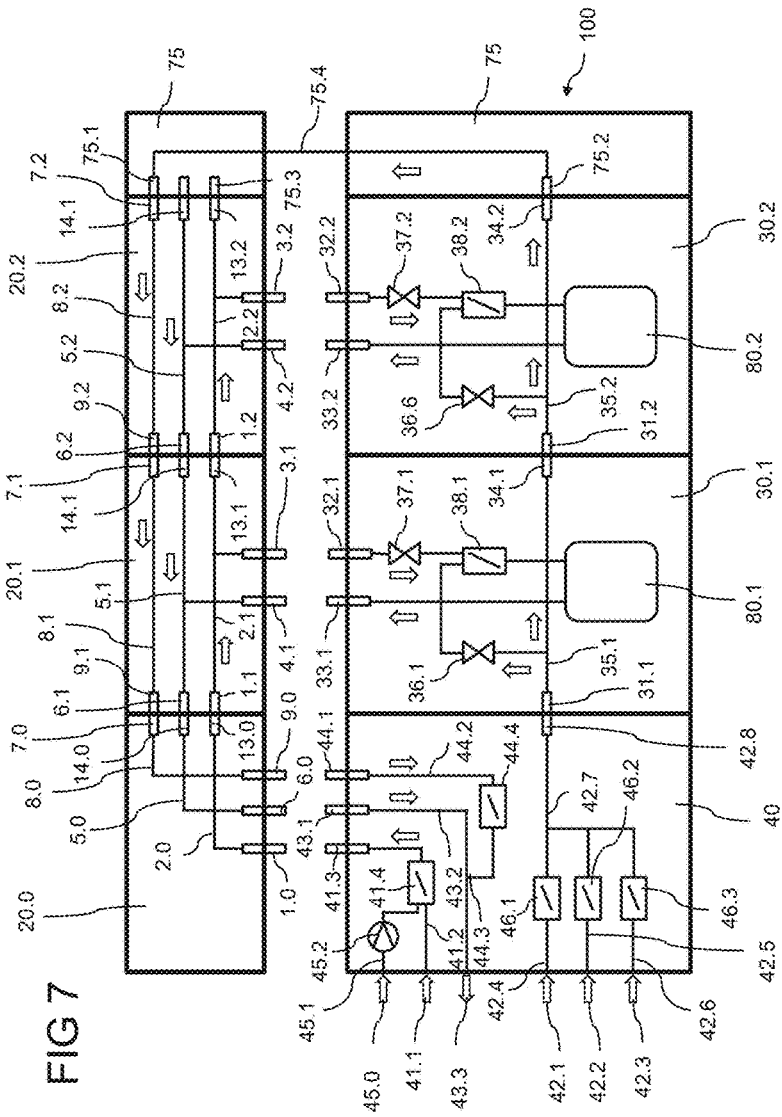
FIG. 7 is a schematic view showing a fourth calibrating station according to the present invention in the assembled state.
Figure 8:
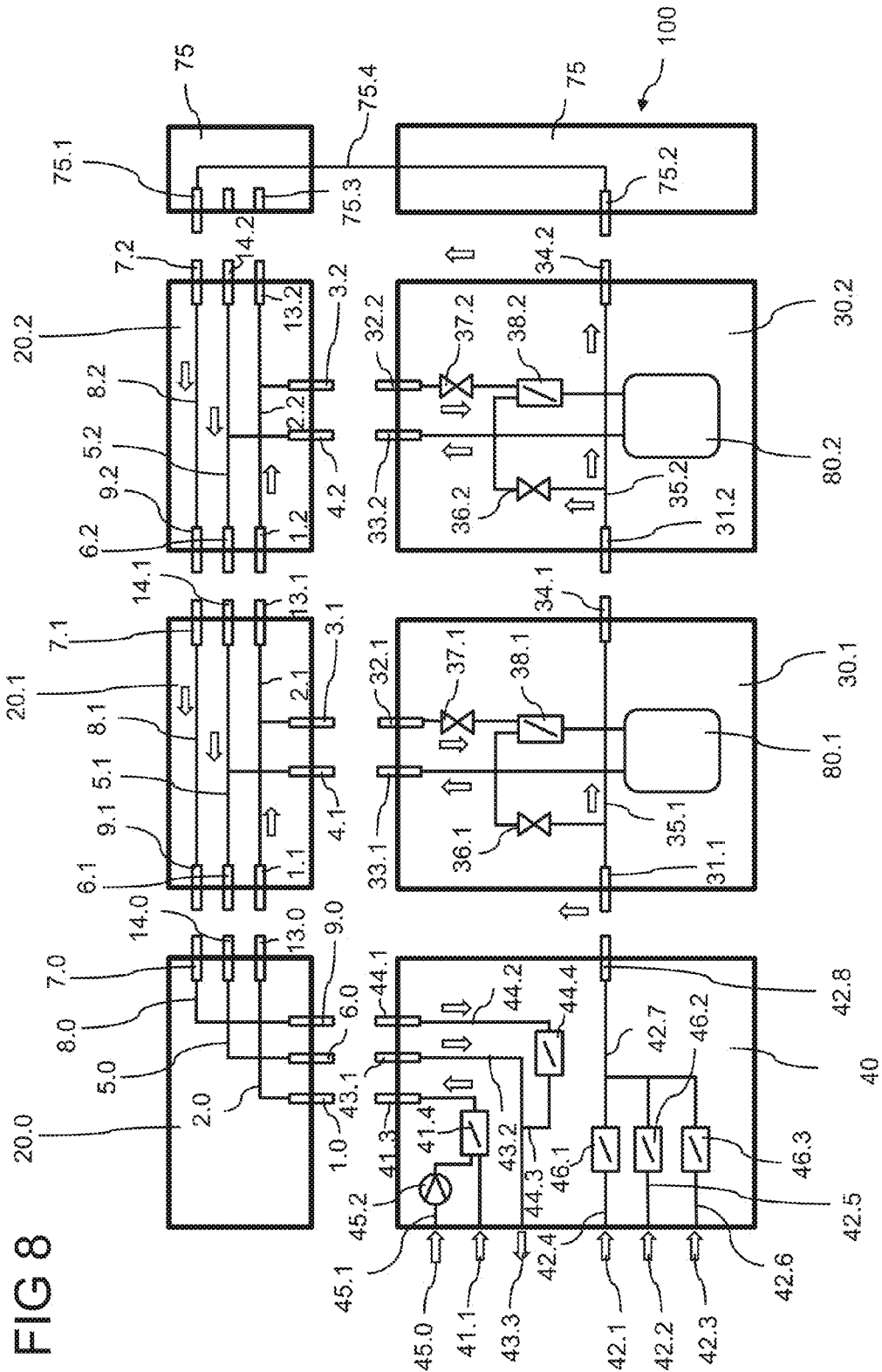
FIG. 8 is a schematic view showing the fourth calibrating station according to FIG. 7 in the disassembled state.

FIGS. 7 and 8 schematically show a fourth calibrating station 100 according to the present invention, once in the assembled state (FIG. 7) and once in the disassembled state (FIG. 8). The structure of the gas routing modules 20.1 through 20.2 corresponds to the structure of the gas routing module 20.1 according to FIG. 5, the structure of the test modules 30.1 and 30.2 corresponds to the structure of the test module 30.1 according to FIG. 6. Besides the gas routing modules 20.1 through 20.2, the calibrating station 100 has a gas routing master module 20.0, which is used for connecting the gas routing modules 20.1 through 20.2 with the master module 40 of the calibrating station 100. The master module 40 is used to control the feed of gases and the discharge of gases to or from the test modules 30.1 and 30.2. The master module 40 has a plurality of test gas inlets 42.1 through 42.3, via which the various test gases can be fed to the master module 40. They are fed together via test gas lines 42.4 through 42.6 in the master module 40 to a common test gas line 42.7. Switches 46.1 through 46.3 are each provided in the test gas lines 42.4 through 42.6 for controlling which test gas is fed through the common test gas line 42.7 to the test modules 30.1 and 30.2. The test gas line 42.7 ends in the test gas outlet 42.8, via which the selected test gas is fed to the adjacent test module 30.1.

The master module 40 further has a fresh gas inlet 41.1, via which fresh gas can be fed to the master module 40. Furthermore, the master module 40 has a first waste gas outlet 43.3 that is used for the disposal of spent test gas/fresh gas and/or for the disposal of unspent test gas. In the master module 40, a first waste gas line 43.2, via which spent test gas/fresh gas is fed back into the test modules 30.1 and 30.2, and a second waste gas line 44.2, via which unspent test gas is fed back into the test modules 30.1 and 30.2, may be brought together by means of a switch for discharge via the first waste gas outlet 43.3. Furthermore, a compressed air inlet 45.0 and a compressed air line 45.1 may be provided in the master module 40, whereby the compressed air line 45.1 is connected via a switch 41.1 with the fresh gas line 41.2 in a gas-communicating manner. As a result of this, compressed air may be fed through all components of the calibrating station 100. In particular, the ducts 2.1 through 2.2, 5.1 through 5.2, 8.1 through 8.2 of the gas routing modules 20.1 and 20.2 of the gas routing element 20, but also those of the test modules 30.1 and 30.2 may be cleaned by the feeding of compressed air. Also, the master module 40 may have a compressed air pump 45.2. The master module is preferably designed such that it is possible to switch back and forth between the compressed air inlet 45.0 and the fresh gas inlet 41.1. The compressed air or fresh air is needed for purging the gas-measuring devices 90.1 and 90.2 after a gassing by means of test gas, among other things. The compressed air or the fresh air is switched to a common so-called fresh gas line in the master module 40. This fresh gas line is fed from the master module 40 via the feed ducts 2.1 and 2.2 of the external gas routing element 20 to the test modules 30.1 and 30.2. The feed ducts 2.1 and 2.2 have branches for feeding fresh gas or compressed air to each test module 30.1 and 30.2. As an alternative or in addition to the compressed air pump 45.2, the master module 40 may have a fresh air pump that is arranged in the fresh gas line 41.2. Depending on whether fresh gas or compressed air shall be fed to the test modules 30.1 and 30.2, it is possible to switch back and forth between the two pumps.

Further, the calibrating station 100 has a closing element 75. This closing element 75 is used so that excess test gas fed through the test modules 30.1 and 30.2 can be fed back to the master module 40 via the gas routing element 20. For this purpose, the closing element 75 has a closing inlet 75.2, via which the excess test gas flows in from the last test module 30.2. The excess test gas is fed via a closing duct 75.3 to the closing outlet 75.1, which is connected in a gas-communicating manner with the third gas inlet opening 7.1 of the last gas routing module 20.2. Further, the closing element 75 has closing mechanisms 75.3 that are used to close the recirculating duct 5.2 as well as the feed duct 2.2 of the last gas routing module 20.2.

FIG. 8 shows the fourth calibrating station according to FIG. 7 in the disassembled state.

Figure 9:
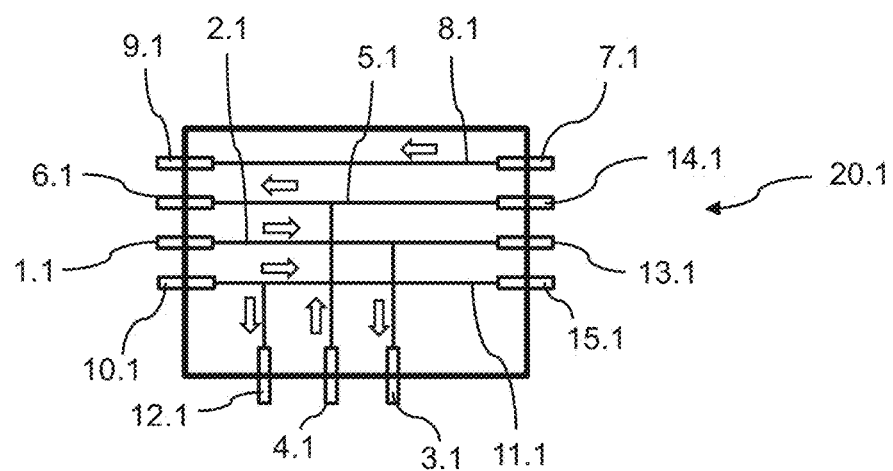
FIG. 9 is a schematic view showing a gas routing module of a second gas routing element.

FIG. 9 schematically shows a gas routing module 20.1 of a second, alternative gas routing element 20. The gas routing module 20.1 has the same gas inlet openings 1.1, 4.1 as well as 7.1, the same gas outlet openings 3.1, 6.1 as well as 9.1 and correspondingly the same feed duct 2.1, the same recirculating duct 5.1 as well as the same third duct 8.1, as the gas routing module 20.1 according to FIG. 5. In addition to the gas routing module 20.1 according to FIG. 5, the gas routing module 20.1 according to FIG. 9 has an additional duct, namely a fourth duct 11.1. This fourth duct 11.1 connects the additional fourth gas inlet opening 10.0 with the additional gas outlet openings 12.1 and 15.1 of the gas routing module 20.1. Test gas can be fed via the gas outlet opening 12.1 to the test module 30.1. Also, test gas can be fed via the gas outlet opening 15.1 to the adjacent gas routing modules 20.2 through 20.*x* and thus to the additional test modules 30.2 through 30.*x*.

Figure 10:
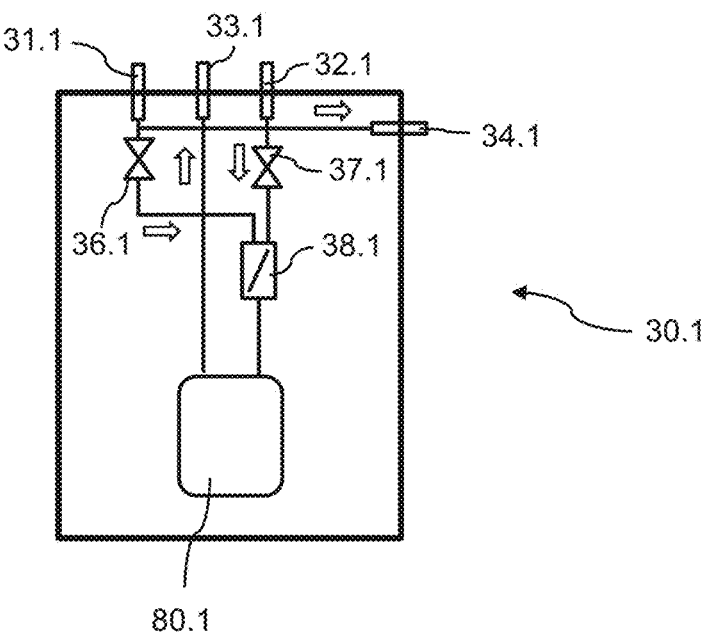
FIG. 10 is a schematic view showing a test module belonging to the gas routing module according to FIG. 9.

FIG. 10 schematically shows a test module 30.1 belonging to the gas routing module 20.1 according to FIG. 9. The test module 30.1 has a test gas inlet opening 31.1 for feeding test gas. The test gas introduced is fed via a first test gas line of the mount 80.1 and via a second test gas line, i.e., a branch of the first test gas line, to an adjacent test module 30.2. Otherwise, the structure of the gas routing module 20.1 corresponds to that of FIG. 6.

Figure 11:
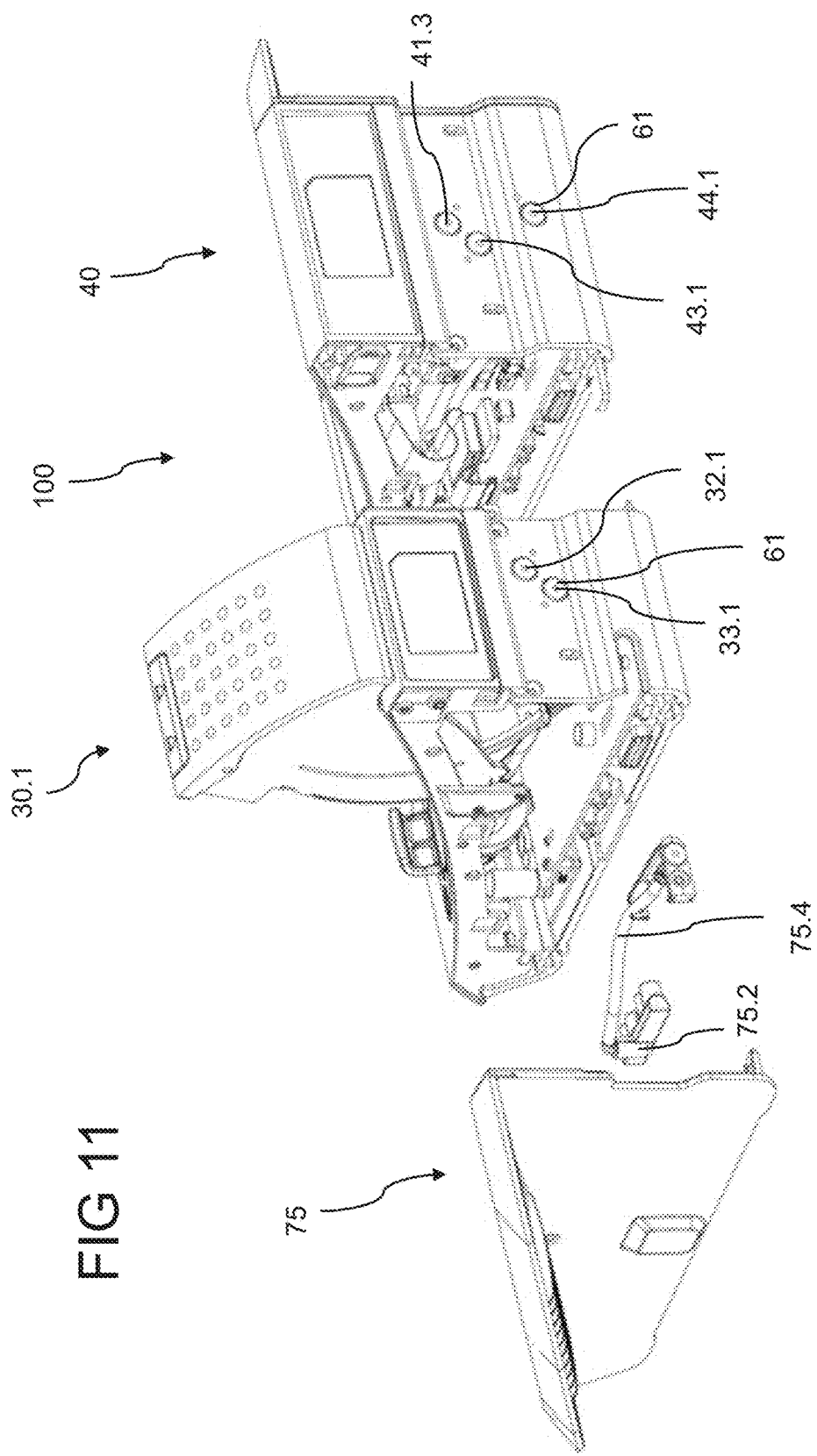
FIG. 11 is a schematic view showing a fifth calibrating station (without gas routing element) in the disassembled state.

FIG. 11 schematically shows a fifth calibrating station 100 (without gas routing element 20) in the disassembled state. A test module 30.1 is arranged next to the master module 40 of the calibrating station 100. A closing element 75 is provided on the other side of the test module 30.1. The test module openings 32.1 and 33.2 of the test module 30.1, which are designed for connecting with the first gas outlet opening 3.1 and the second gas inlet opening 4.1 of a gas routing element 20, which is not shown, and a gas routing module 20.1 of a gas routing element 20, can be readily recognized. Fresh gas can be fed via the test module opening 32.1 to the test module 30.1. The test module opening 33.2 is used for recirculating spent test gas or fresh gas into a gas routing element 20 or the gas routing module 20.1 of a gas routing element 20. The master module 40 has a corresponding fresh gas outlet 41.3, a first waste gas inlet 43.1 as well as a second waste gas inlet 44.1. Sealing elements 61, in particular O-ring seals made of a fluorinated rubber, are provided at the test module openings 32.1 and 33.2 of the test module 30.1 as well as the fresh gas outlet 41.3, the first waste gas inlet 43.1 as well as the second waste gas inlet 44.1 of the master module 40. These are used for the gastight connection of the test module 30.1 to the gas routing element 20, not shown.

Figure 12:
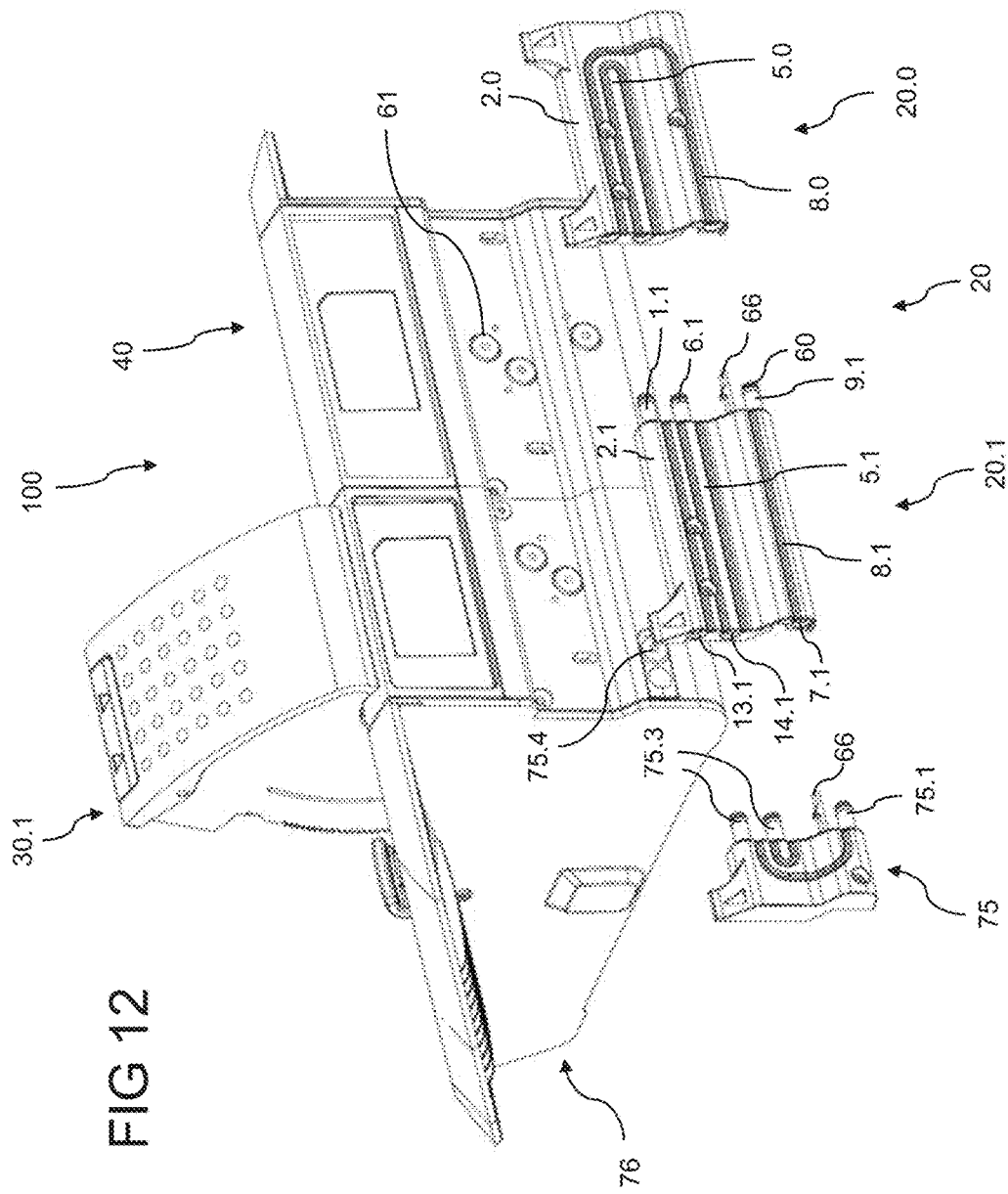
FIG. 12 is a schematic view showing the fifth calibrating station according to FIG. 11 in the assembled state with a disassembled gas routing element.

FIG. 12 shows the fifth calibrating station 100 according to FIG. 11 in the assembled state with a disassembled gas routing element 20. The gas routing element 20 has a gas routing master module 20.0 as well as a gas routing module 20.1. The gas routing master module 20.0 is used for connecting the gas routing element 20 to the master module 40 of the calibrating station 100. The gas routing master module 20.0 has a feed duct 2.0 for feeding fresh gas from the master module 40 to the test modules 30.1 and 30.2, a recirculating duct 5.0 for feeding back spent fresh gas or test gas from the test modules 30.1 and 30.2 to the master module 40 as well as a third duct 8.0 for feeding back unspent test gas to the master module 40. The gas routing module 20.1 has corresponding openings 1.1, 6.1, 9.1, 13.1 and ducts 2.1, 5.1 and 8.1 to feed the gases to or from the test modules 30.1 and 30.2. A closing element 75 is arranged at the gas routing module 20.1 to close the feed duct 2.1 as well as the recirculating duct 5.1 of the gas routing module 20.1, on the one hand, and, on the other hand, to make possible a recirculation of the unspent test gas via the closing duct 75.4 of the closing element 75 in the third duct 8.1 of the gas routing module 20.1. The openings of the gas routing master module 20.0 as well as those of the gas routing module 20.1 and of the closing element 75 are designed as plug-type connecting elements, i.e., either as plugs, male part, or as plug mounts, female part. Sealing elements, in particular in the form of O-ring seals, are provided at the plug-type connecting elements. Further, sealing elements 61, in particular O-ring seals made of a fluorinated rubber, are provided at the test module openings 32.1 and 33.1 as well as the fresh gas outlet 41.3, the first waste gas inlet 43.1 and the second waste gas inlet 44.1 of the master module 40 and the end of the closing duct 75.4. A cover 76 may be provided for the partial covering of the gas routing module 20.1 as well as of the closing element 75. The gas routing master module 20.0, the gas routing module 20.1 as well as the closing element 75 advantageously have fastening elements 66, which are used for fastening these components to one another. The fastening elements 66 guarantee that the components of the gas routing element 20 can be fastened to one another rigidly and securely in a gas-communicating manner and in particular in a gastight manner. The fastening elements 66 guarantee a high stability of the gas routing element 20 even in large configurations, i.e., of a high number of gas routing modules 20.1 through 20.x. Preferably, the fastening elements 66 are designed as locking hooks and locking hook mounts.

Figure 13:
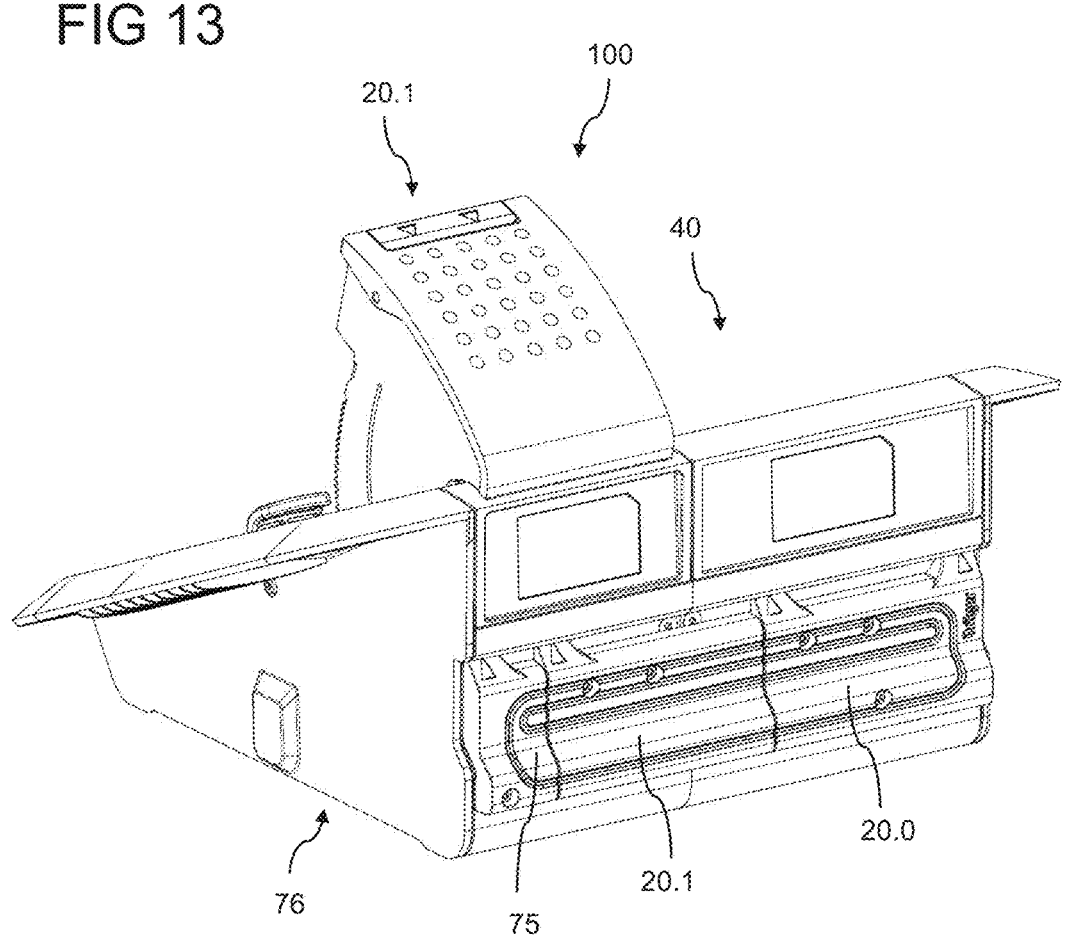
FIG. 13 is a schematic view showing the fifth calibrating station in the assembled state.

The fifth calibrating station 100 according to FIG. 12 is completely assembled in FIG. 13.

Figure 14:
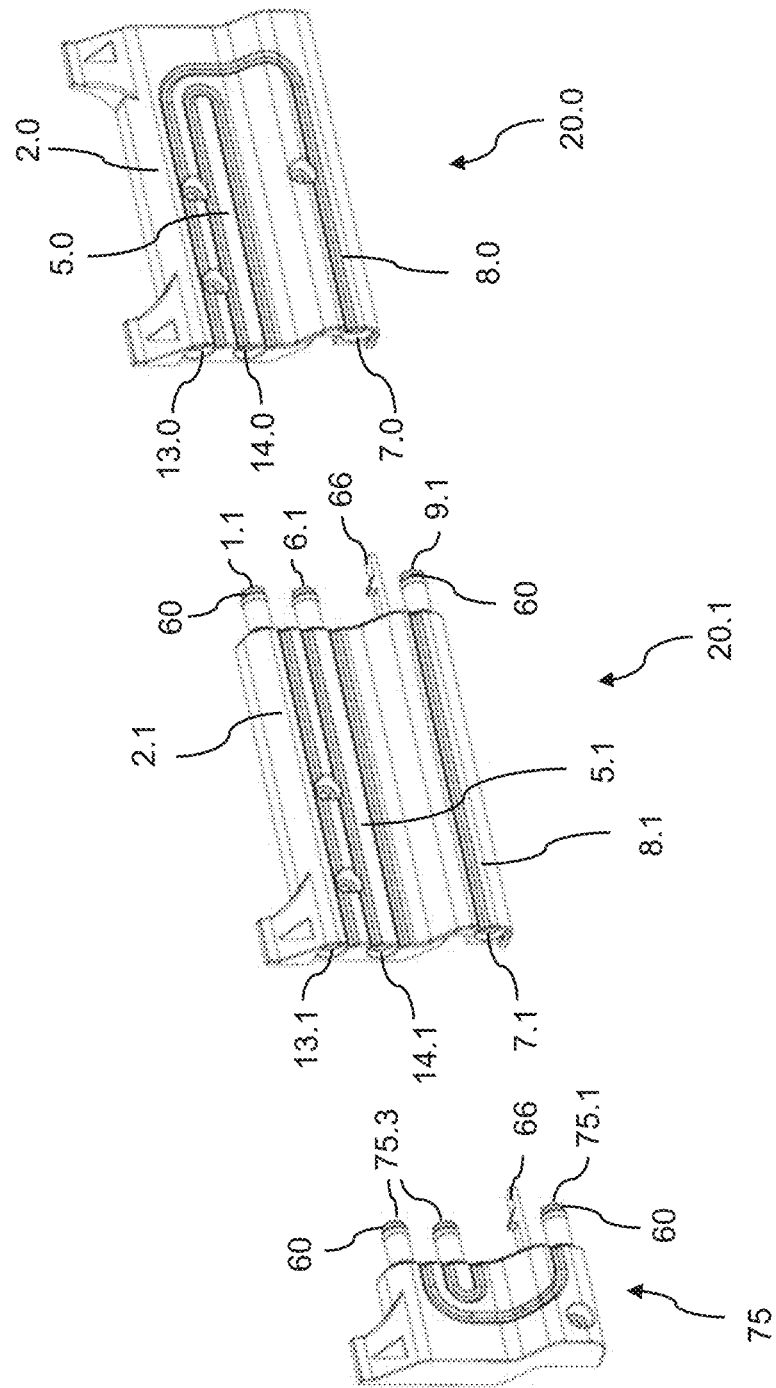
FIG. 14 is a schematic view showing the disassembled gas routing element of the fifth calibrating station.

FIG. 14 schematically shows the disassembled gas routing element 20 of the fifth calibrating station 100.

Figure 15:
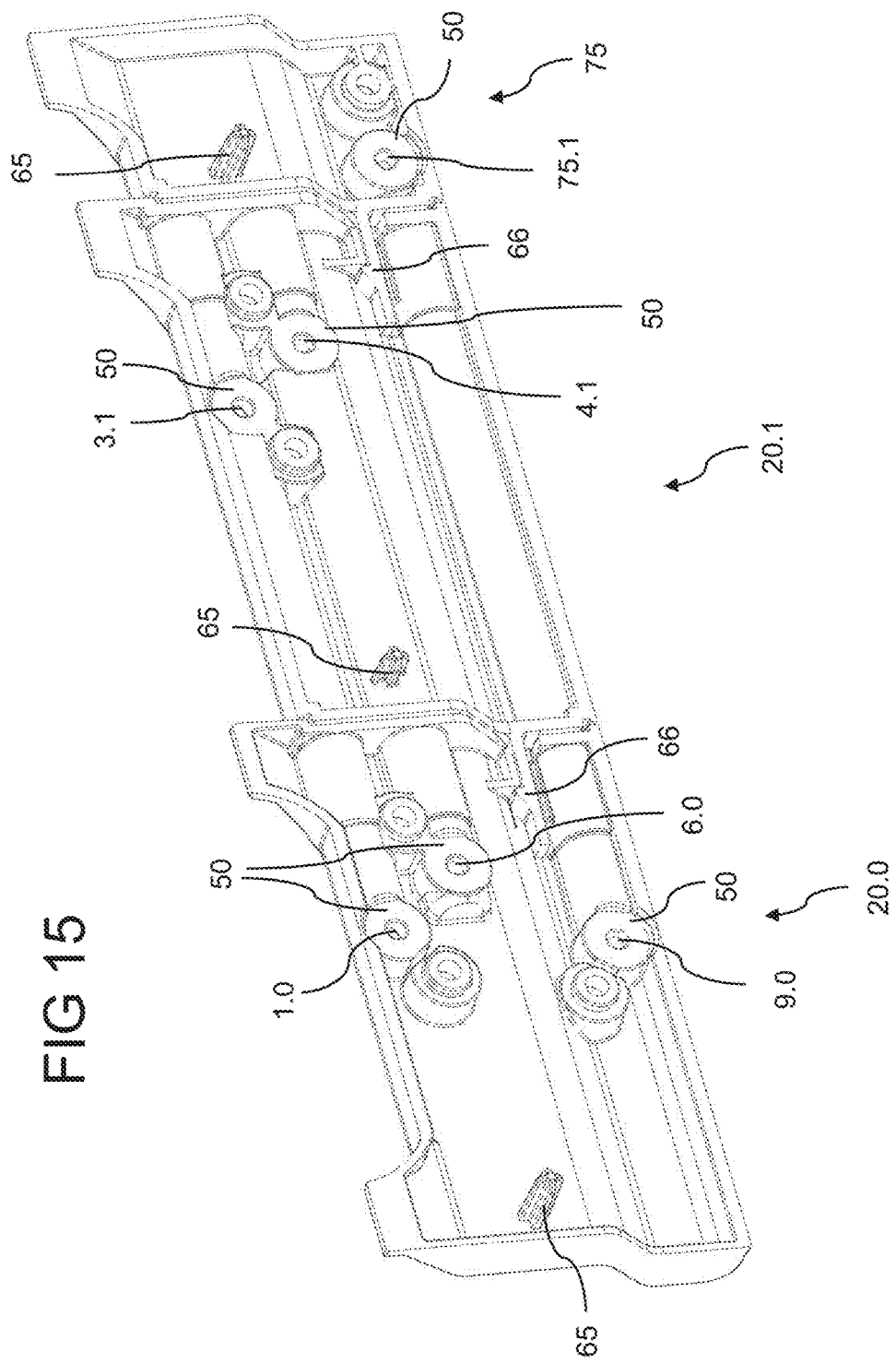
FIG. 15 is a schematic view showing the assembled gas routing element of the fifth calibrating station.

FIG. 15 schematically shows the assembled gas routing elements 20 of the fifth calibrating station 100. On the side facing the master module 40 and the test module 30.1, the gas routing element 20 has locking mechanisms 65 in the form of crossribs. These crossribs mesh with corresponding openings in the master module 40 and the test module 30.1. Via these crossribs 65, individual test modules 30.1 or the master module 40 are prevented from being able to be pulled apart from each other. This increases the reliability of the calibrating station 100. In addition, a gas routing element 20 may have sealing surfaces for sealing elements 61 of the master module 40 and/or test modules 30.1 through 30.x. As a result of this, the sealing between the components can be further improved. It is obvious from FIG. 15 how the fastening elements of the components 20.0, 20.1 and 75 of the gas routing element 20 mesh with one another in order to fasten these components 20.0, 20.1 and 75 to one another in a secure and exactly gastight manner.

The above explanation of the embodiments describes the present invention exclusively within the framework of examples. Of course, individual features of the embodiments, insofar as technically useful, may be freely combined with one another without going beyond the scope of the present invention.

While specific embodiments of the invention have been shown and described in detail to illustrate the application of the principles of the invention, it will be understood that the invention may be embodied otherwise without departing from such principles.

APPENDIX

LIST OF REFERENCE NUMBERS 1.0-1.x First gas inlet openings
2.0-2.x Feed ducts/Feed ducts for fresh gas
3.1-3.x First gas outlet openings
4.1-4.x Second gas inlet openings
5.0-5.x Recirculating ducts/Recirculating ducts for spent test gas
6.0-6.x Second gas outlet openings
7.0-7.x Third gas inlet openings
8.0-8.x Third ducts/Recirculating ducts for unspent test gas
9.0-9.x Third gas outlet openings
10.0-10.x Fourth gas inlet openings
11.0-11.x Fourth ducts/Feed ducts for test gas
12.0-12.x Fourth gas outlet openings
13.0-13.x First gas outlet openings
14.0-14.x Second gas inlet openings
15.0-15.x Fourth gas outlet openings
20 Gas routing element
20.0 Gas routing master module
20.1-20.x Gas routing modules
30.1-30.x Test modules
31.1-31.x Test module openings/Test gas inlet openings
32.1-32.x Test module openings
33.1-33.x Test module openings
34.1-34.x Test module openings/Test gas outlet openings
35.1-35.x Test gas ducts
36.1-36.x Valve devices
37.1-37.x Switching devices
38.1-38.x Valve devices
40 Master module
41.1 Fresh gas inlet
41.2 Fresh gas line
41.3 Fresh gas outlet
41.4 Switch
42.1-42.3 Test gas inlets
42.4-42.7 Test gas lines
42.8 Test gas outlet
43.1 First waste gas inlet
43.2 First waste gas line
43.3 First waste gas outlet
44.1 Second waste gas inlet
44.2 Second waste gas line 44.3 Second waste gas outlet
45.0 Compressed air inlet
45.1 Compressed air line
45.2 Compressed air pump
46.1-46.3 Switches
50 Sealing surfaces for sealing elements
60 Sealing elements
61 Sealing elements
65 Locking mechanism
66 Fastening elements
70 Fastening means
75 Closing element
75.1 Closing outlet
75.2 Closing inlet
75.3 Closing mechanisms
75.4 Closing duct
76 Cover
80.1-80.x Mounts for gas-measuring devices
90.1-90.x Gas-measuring device
100 Calibrating station

What is claimed is:

1. A gas routing element for gassing at least one gas-measuring device, whereby each gas-measuring device can be arranged in a test module of a calibrating station for gas-measuring devices and the gas routing element is a structurally fixed component external to the test modules, the gas routing element comprising:
 a first gas inlet opening;
 a feed duct connected with the first gas inlet opening in a gas-communicating manner;
 two first gas outlet openings connected with the feed duct in a gas-communicating manner;
 two second gas inlet openings;
 a recirculating duct connected with the second gas inlet openings in a gas-communicating manner;
 a second gas outlet opening connected with the recirculating duct in a gas-communicating manner; and
 a fastening means for fastening the gas routing element to at least one of the calibrating station and the test module of the calibrating station, wherein the first gas inlet opening, the two first gas outlet openings, the two second gas inlet openings and the second gas outlet opening are configured as sealing plug connecting elements.

2. A gas routing element in accordance with claim 1, further comprising:
 a third gas inlet opening;
 a third duct connected with the third gas inlet opening in a gas-communicating manner; and
 a third gas outlet opening connected with the third duct in a gas-communicating manner.

3. A gas routing element in accordance with claim 2, further comprising:
 a fourth gas inlet opening;
 a fourth duct connected with the fourth gas inlet opening in a gas-communicating manner; and
 two fourth gas outlet openings connected with the fourth duct in a gas-communicating manner.

4. A gas routing element in accordance with claim 1, wherein the gas routing element comprises a continuous gas routing module for fastening to the calibrating station and at least via the first gas outlet openings and the second gas inlet openings defining a parallel connection for gassing of a plurality of test modules.

5. A gas routing element in accordance with claim 4, in combination with a master module of the calibrating station wherein the first gas inlet opening and the second gas outlet opening connect with the master module of the calibrating station in a gas-communicating manner.

6. A gas routing element in accordance with claim 5, wherein the gas routing element comprises a plurality of gas routing modules including a first gas routing module comprising the first gas inlet opening, the feed duct, the two first gas outlet openings, the two second gas inlet openings, the recirculating duct, and the second gas outlet opening and including at least one additional gas routing module, each additional gas routing module comprising:
 an additional module first gas inlet opening;
 an additional module first gas outlet opening
 an additional module second gas outlet opening to communicate with the first gas routing module;
 an additional module second gas inlet opening to a subsequent additional gas routing module for connecting the plurality of gas routing modules in a gas-communicating manner to one another, each first gas outlet opening of the plurality of gas routing modules has the first gas outlet opening and the second gas inlet opening for connecting with an associated test module in a gas-communicating manner.

7. A gas routing element in accordance with claim 6, further comprising a gas routing master module for connecting in a gas-communicating manner with the calibrating station master module and for connecting to one or more of the plurality of gas routing modules, wherein the gas routing master module comprises:
 two gas inlet openings;
 two gas outlet openings;
 a feed duct;
 a recirculating duct connecting a gas inlet opening with a gas outlet opening in a gas-communicating manner.

8. A gas routing element in accordance with claim 6, further comprising sealing elements comprising O-ring seals for a gastight connection of the gas routing element to the calibrating station or between two adjacent gas routing modules gas inlet opening and gas outlet opening.

9. A gas routing element in accordance with claim 6, further comprising a locking mechanism for positioning the gas routing element at the calibrating station or positioning the gas routing modules and the gas routing master modules have fastening elements for fastening to one another.

10. A gas routing element in accordance with claim 1, further comprising a closing element for closing the one or more of the ducts or connecting a test module with the gas routing element in a gas-communicating manner.

11. A calibrating station for calibrating gas-measuring devices, the calibrating station comprising:
 a gas routing element comprising a first gas inlet opening, a feed duct connected with the first gas inlet opening in a gas-communicating manner, two first gas outlet openings connected with the feed duct in a gas-communicating manner, two second gas inlet openings; a recirculating duct connected with the second gas inlet openings in a gas-communicating manner, a second gas outlet opening connected with the recirculating duct in a gas-communicating manner and a fastening means for fastening the gas routing element to at least another portion of the calibrating station;
 a plurality of test modules arranged in a series relative to each other, each test module comprising a mount for a gas-measuring device and test module openings for connecting the test modules with the gas routing element in a gas-communicating manner, wherein the test module openings, the gas inlet openings and the gas outlet openings of the gas routing element and/or the fresh gas inlet, the fresh gas outlet, the test gas inlets, the test gas outlet, the first waste gas inlet, the first waste gas outlet, the second waste gas inlet and the second waste gas outlet of the master module are designed as sealing plug connecting elements.

12. A calibrating station in accordance with claim 11, further comprising:
a master module for controlling the gassing of the calibrating station, the master module comprising:
a fresh gas inlet;
a fresh gas line;
a fresh gas outlet for feeding fresh gas to the test modules;
a test gas inlet;
a test gas line;
a test gas outlet for feeding at least one test gas to the test modules;
a waste gas inlet;
a waste gas line; and
a first waste gas outlet for recirculating spent test gas from the test modules through the master module.

13. A calibrating station in accordance with claim 12, wherein the routing element further comprises:
a third gas inlet opening;
a third duct connected with the third gas inlet opening in a gas-communicating manner;
a third gas outlet opening connected with the third duct in a gas-communicating manner.
a fourth gas inlet opening;
a fourth duct connected with the fourth gas inlet opening in a gas-communicating manner; and
two fourth gas outlet openings connected with the fourth duct in a gas-communicating manner, wherein:
the feed duct of the gas routing element feeds fresh gas to the test modules;
the fourth duct feeds test gas to the test modules;
the recirculating duct recirculates spent test gas from the test modules; and
the third duct recirculates unspent test gas from the test modules.

14. A calibrating station in accordance with claim 12, further comprising sealing elements comprising O-ring seals for a gastight connection of at least one of the test modules to the gas routing element and the test modules to the master module and between the master module and the gas routing element to the test module openings and to the fresh gas outlet and to the test gas outlet and to the first waste gas inlet and to the second waste gas inlet.

15. A calibrating station in accordance with claim 12, wherein the master module further comprises a compressed air inlet and a compressed air line, wherein the compressed air line is connected with the fresh gas line in a gas-communicating manner via a switch.

16. A calibrating station in accordance with claim 12, wherein at least one of the test modules and the master module have locking countermechanisms for positioning the gas routing element at the calibrating station.

17. A calibrating station in accordance with claim 11, wherein a length of the gas routing element can be adapted to a number and size of the test modules.

18. A calibrating station in accordance with claim 11, wherein the gas routing element comprises a plurality of gas routing modules including a first gas routing module comprising the first gas inlet opening, the feed duct, the two first gas outlet openings, the two second gas inlet openings, the recirculating duct, and the second gas outlet opening and including at least one additional gas routing module, each additional gas routing module comprising:
an additional module first gas inlet opening;
an additional module first gas outlet opening
an additional module second gas outlet opening to communicate with the first gas routing module;
an additional module second gas inlet opening to a subsequent additional gas routing module for connecting the plurality of gas routing modules in a gas-communicating manner to one another, each first gas outlet opening of the plurality of gas routing modules has the first gas outlet opening and the second gas inlet opening for connecting with an associated test module in a gas-communicating manner and wherein each gas routing module is provided per each test module.

19. A calibrating station in accordance with claim 11, wherein for feeding test gas to the test modules, the test modules each comprise a test gas inlet opening, a test gas duct and a test gas outlet opening, whereby the test gas outlet opening of each test module is connected with the test gas inlet opening of an adjacent test module in a gas-communicating manner.

20. A gas routing element for gassing at least one gas-measuring device, whereby each gas-measuring device can be arranged in a test module of a calibrating station for gas-measuring devices and the gas routing element is a structurally fixed component external to the test modules, the gas routing element comprising:
a first gas inlet opening;
a feed duct connected with the first gas inlet opening in a gas-communicating manner;
two first gas outlet openings connected with the feed duct in a gas-communicating manner;
two second gas inlet openings;
a recirculating duct connected with the second gas inlet openings in a gas-communicating manner;
a second gas outlet opening connected with the recirculating duct in a gas-communicating manner; and
a fastening means for fastening the gas routing element to at least one of the calibrating station and the test module of the calibrating station, wherein a length of the gas routing element can be configured to a number and size of test modules.

\* \* \* \* \*